United States Patent
Kawano et al.

(10) Patent No.: US 6,605,735 B2
(45) Date of Patent: Aug. 12, 2003

(54) RUTHENIUM COMPLEX, PROCESS FOR PRODUCING THE SAME AND PROCESS FOR PRODUCING THIN FILM

(75) Inventors: Kazuhisa Kawano, Yokohama (JP); Kenichi Sekimoto, Sagamihara (JP); Noriaki Oshima, Yokohama (JP); Tetsuo Shibutami, Sagamihara (JP); Shuji Kumagai, Sagamihara (JP); Taishi Furukawa, Yokohama (JP)

(73) Assignee: Tosoh Corporation, Yamaguchi (JP)

(*) Notice: Subject to any disclaimer, the term of this patent is extended or adjusted under 35 U.S.C. 154(b) by 0 days.

(21) Appl. No.: 10/236,914

(22) Filed: Sep. 9, 2002

(65) Prior Publication Data

US 2003/0088116 A1 May 8, 2003

(30) Foreign Application Priority Data

| Sep. 12, 2001 | (JP) | P.2001-276478 |
| Sep. 12, 2001 | (JP) | P.2001-276479 |
| Sep. 12, 2001 | (JP) | P.2001-276480 |
| Sep. 12, 2001 | (JP) | P.2001-276481 |
| Nov. 26, 2001 | (JP) | P.2001-359769 |
| Mar. 20, 2002 | (JP) | P.2002-078970 |

(51) Int. Cl.$^7$ ............... C07F 17/02; C23C 16/00; C23C 14/26
(52) U.S. Cl. ............... 556/136; 427/248.1; 427/587; 427/593
(58) Field of Search ............... 556/136; 427/587, 427/248.1, 593

(56) References Cited

U.S. PATENT DOCUMENTS

| 4,927,670 A | 5/1990 | Erbil ............... 427/255.3 |
| 4,992,305 A | 2/1991 | Erbil ............... 427/252 |
| 5,130,172 A | 7/1992 | Hicks et al. ............... 427/252 |
| 5,352,488 A | 10/1994 | Spencer et al. ............... 427/250 |
| 5,403,620 A | 4/1995 | Kaesz et al. |
| 5,962,716 A | 10/1999 | Uhlenbrock et al. ............... 556/16 |
| 6,002,036 A | 12/1999 | Kadokura ............... 556/136 |
| 6,063,705 A | 5/2000 | Vaartstra ............... 438/681 |
| 6,207,232 B1 | 3/2001 | Kadokura ............... 427/252 |
| 6,380,080 B2 | 4/2002 | Visokay ............... 438/681 |

FOREIGN PATENT DOCUMENTS

| JP | 5-132776 A | 5/1993 |
| JP | 6-283438 A | 10/1994 |
| JP | 11-35589 A | 2/1999 |
| JP | 2000-212744 A | 8/2000 |
| JP | 2000-281694 A | 10/2000 |
| JP | 2001-172294 A | 6/2001 |

OTHER PUBLICATIONS

Cox et al., Organometallics, vol. 4, No. 11, pp. 2001–2005 (1985).*
Cox et al., Journal of Organometallic Chemistry, vol. 438, pp. 195–207 (1992).*
Ketkov et al., Journal of Organometallic Chemistry, vol. 563, pp. 209–217 (1998).*
Wimonrat Trakarnpruk et al., Protonation of [Ru(C$_5$Me$_5$) (3–C$_6$H$_9$)] (C$_6$H$_9$) = methylpentadienyl): Fluctionality and Structure of an Agostic Complex, Inorganica Chimica Acta. 259, 197 (1997).
Rolf Gleiter et al., "Half–Open Metallocenes" of Iron, Ruthenium, and Osmium: Synthesis, Characterization, Photoelectron Spectroscopy, and Theoretical Calculations, Organometallics, 8, 298 (1989).
David No. Cox et al., 152. Preparation of Ru(CO)(diene)$_2$ Complexes by Electron–Beam Evaporation of Ruthenium, Helv. Chim. Acta, 67, 1365 (1984).
Domenico Minniti et al., The Reaction of Ruthenium Atoms with Buta–1, 3–Diene: Synthesis of [RuL($\eta^4$–C$_4$H$_6$)$_2$] WHERE L = PF$_3$, CO AND (CH$_3$)$_3$ CNC, J. Organomet Chem., 258, C12 (1983).

* cited by examiner

Primary Examiner—Porfirio Nazario-Gonzalez
(74) Attorney, Agent, or Firm—Sughrue Mion, PLLC

(57) ABSTRACT

A ruthenium-containing thin film is produced by the chemical vapor deposition method etc. with the use of an organometallic ruthenium compound represented by the general formula (1), specific example of which is (2,4-dimethylpentadienyl)(ethylcyclopentadienyl)ruthenium:

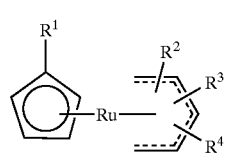

(1)

or an organometallic ruthenium compound represented by the general formula (7), specific example of which is carbonylbis(2-methyl-1,3-pentadiene)ruthenium:

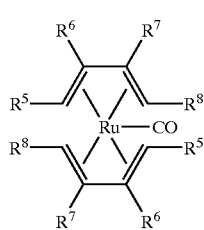

(7)

as the precursor.

26 Claims, 12 Drawing Sheets

RUTHENIUM COMPLEX, PROCESS FOR PRODUCING THE SAME AND PROCESS FOR PRODUCING THIN FILM

FIELD OF THE INVENTION

This invention relates to organometallic ruthenium complexes which are useful for forming a ruthenium-containing thin film by the chemical vapor deposition method (hereinafter referred to as the CVD method), the coating heat decomposition method and so on, a process for producing the same and a process for producing a ruthenium-containing thin film to be used in electronics devices such as semiconductor memories.

BACKGROUND OF THE INVENTION

With the progress of fine processing in memory cells in association with the recent tendency toward highly integrated semiconductor memory devices, attempts have been made to use ferroelectric thin films such as $(Ba,Sr)TiO_3$ as insulating films in capacitors. In capacitors provided with ferroelectric thin films, use is made of noble metals such as Pt, Ru and Ir as electrodes. Among these metals, Ru is expected as the most useful electrode material, since its oxide has a conductivity and excellent fine processing properties. Thus, examinations have been made on electrodes made of an Ru thin film or an $RuO_2$ thin film. To form such ruthenium-containing thin films in highly integrated memory devices, the CVD method is the most suitable since it is excellent in step coverage and composition controlling.

It is considered that organometallic compounds, which have low melting point and can be easily handled among metal compounds, are adequate as precursors for forming thin films by this CVD method. As organometallic compounds for the deposition of ruthenium or ruthenium oxide thin films, it has been a practice to use ruthenocene or tris(dipivaloylmethanato)ruthenium (hereinafter referred to as $Ru(DPM)_3$) [Japanese Patent Laid-Open No. 283438/1994]] or tris(octane-2,4-dionato)ruthenium (hereinafter referred to as $Ru(OD)_3$) [Japanese Patent Laid-Open No. 2000-212744]. Ruthenocence has a sandwich structure carrying ruthenium sandwiched between two cyclopentadienyl rings each consisting exclusively of carbon and hydrogen. Because of being highly stable in the atmosphere and having no toxicity, ruthenocene is suitable as a CVD precursor. However, it suffers from difficulties in the vaporization of the precursor and transportation onto substrates somewhat, since it is in the state of a solid at ordinary temperature and has a relatively high melting point of about 200° C.

Accordingly, studies have been vigorously made in recent years on ruthenium compounds having lower melting point. The melting point of a ruthenium-containing organometallic compound can be lowered by converting it into a ruthenocene derivative in which at least one of the hydrogen atoms in the cyclopentadienyl rings of ruthenocene is substituted by an alkyl group such as a methyl or ethyl group. For example, Japanese Patent Laid-Open No. 35589/1999 discloses bis(alkylcyclopentadienyl)ruthenium typified by bis(ethylcyclopentadienyl)ruthenium (hereinafter referred to as $Ru(EtCp)_2$) and bis(isopropylcyclopentadienyl) ruthenium as a ruthenocene derivative. Further, Japanese Patent Laid-Open No. 2000-281694 discloses use of alkyl-substituted ruthenocenes as CVD precursors. It is stated that each of these organometallic compounds is in the state of a liquid at ordinary temperature and has a lower melting point than ruthenocene, i.e., having characteristics required as precursors suitable for the CVD method. However, these bis(alkylcyclopentadienyl)rutheniums fundamentally have the ruthenocene structure. Since this structure has an extremely high stability, these complexes have high decomposition points. Therefore, it is essentially needed to elevate the substrate temperature to a high level in the step of film-formation, which results in a problem of worsening in the step coverage.

On the other hand, R. Gleiter et al. (Organometallics, 8, 298 (1989)) reported (cyclopentadienyl)(2,4-dimethylpentadienyl)ruthenium as an example of the synthesis of a half-sandwich complex having a cyclopentadienyl group as a ligand. However, this complex cannot be considered as suitable as a CVD precursor, since it has a melting point of 136 to 137° C. and occurs as a solid at ordinary temperature. There has been reported no case of synthesizing a half-sandwich ruthenium complex which is in the state of a liquid at room temperature and shows excellent vaporization properties.

To synthesize a half-sandwich ruthenocene, it has been a common practice to add a pentadiene derivative, a cyclopentadiene derivative, zinc and halogenated ruthenium hydrate to an appropriate solvent at once and then reacting under appropriate reaction conditions. However, this method is not practically usable since only an extremely low yield can be achieved thereby. As the post-treatment following the reaction, it has been also a practice that the liquid reaction mixture is concentrated to give a pasty mixture and the target product is extracted from the pasty mixture with the use of an appropriate solvent followed by purification by filtration through celite or column chromatography using an alumina column to thereby give the target product. However, this method involves industrially unfavorable steps such as the extraction from the pasty mixture obtained by concentration after the completion of the reaction and the celite-filtration or the column chromatography. To make half-sandwich organometallic ruthenium compounds industrially advantageous, therefore, it has been urgently required to establish a production process whereby a target product can be obtained in a stable state at a high yield.

On the other hand, film-formation by the coating heat decomposition method has been applied to the production of elements having a relatively low integration level. Since precursors to be used in the coating heat decomposition method are dissolved in organic solvents before using to thereby control the film thickness, it is favorable that these precursors are soluble in organic solvents and decompose at low temperature. However, there have been few ruthenium compounds having the above characteristics.

There has been known no carbonylbis(diene)ruthenium complex other than carbonylbis(1,3-butadiene)ruthenium (D. Minniti and P. L. Timms, J. Organomet. Chem., 258, C12(1983)), carbonylbis(2,3-dimethyl-1,3-butadiene) ruthenium and carbonylbis(1,3-cyclohexadiene)ruthenium (D. N. Cox and R. Roulet, Helv. Chim. Acta, 67, 1365 (1984)). These complexes are produced by a process with a need for a reaction at a low temperature, i.e., reacting Ru with a diene at −196° C. and then adding CO.

In the CVD method, a complex employed as a thin film precursor should be supplied as a gas. Among the complexes employed hitherto, $Ru(DPM)_3$ is to be vaporized by sublimation because of its high melting point of 168° C. In the vaporization by sublimation, there arises a problem that the precursor gas concentration varies depending on changes in the surface area of the solid and thus the precursor gas cannot be stably supplied. To overcome this problem, Japanese Patent Laid-Open No. 132776/1993 proposes a method wherein a complex is dissolved in an organic solvent before using. However, the precursor can be not always supplied stably by this method too, since there arise some problems that the solvent alone is vaporized or the solid is deposited due to a difference in vaporization properties between the solvent and the complex. On the other hand, Ru(OD)$_3$ and Ru(EtCp)$_2$ suffer from no problem in the stable supply of the precursors, since they each occurs as a liquid at room temperature and has a relatively high vapor pressure. In these complexes, however, Ru is stably bonded to the respective organic ligands. Thus, these complexes are hardly decomposed and should be treated at a high temperature for the film-formation.

SUMMARY OF THE INVENTION

The present invention aims at providing ruthenium complexes which can be subjected to the film-formation by the CVD method at a low temperature compared with the complexes as described above and can suitably supply a precursor thereof, a process for producing the same and a process for producing a ruthenium-containing thin film.

The present inventors have conducted intensive studies to overcome the above-described problems. As a result, they have found out that the decomposition temperature of a known compound having the ruthenocene structure can be lowered by substituting one of the cyclopentadienyl rings (hereinafter referred to as Cp rings) by linear pentadienyl. As the results of the subsequent studies, they have successfully developed novel ruthenium complexes, which show such a melting point as occurring as a liquid at room temperature and have favorable vaporization properties and decomposition properties, by introducing a lower alkyl group into the Cp rings. They have furthermore found out that the above-described objects can be established by carbonylbis(diene) ruthenium complexes having a low-molecular weight diene and a carbonyl group as a ligand, thereby completing the present invention.

Accordingly, the present invention provides a half-sandwich organometallic ruthenium compound characterized by being represented by the following general formula (1):

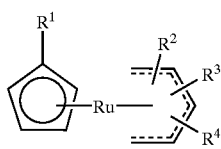
(1)

wherein $R^1$, $R^2$, $R^3$ and $R^4$ are the same or different and each represents hydrogen, a halogen atom, a lower acyl group, a lower alkoxy group, a lower alkoxycarbonyl group or a lower alkyl group, provided that the case where $R^1$ to $R^4$ are all hydrogen, and the case where $R^1$ is hydrogen, one of $R^2$ to $R^4$ is hydrogen, and the remainder are methyl groups are excluded.

The present invention further provides a process for producing a ruthenium-containing thin film characterized by using the above-described half-sandwich organometallic ruthenium compound as the precursor and forming a ruthenium-containing thin film on a heated substrate by the chemical vapor deposition method.

The present invention further provides a process characterized by reacting an open ruthenocene represented by the following general formula (3):

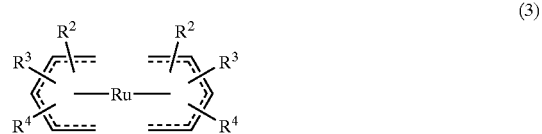
(3)

wherein $R^2$, $R^3$ and $R^4$ are the same or different and each represents hydrogen, a halogen atom, a lower acyl group, a lower alkoxy group, a lower alkoxycarbonyl group or a lower alkyl group;
in a solvent in the presence of zinc with a cyclopentadiene represented by the following general formula (4):

(4)

wherein $R^1$ represents hydrogen, a halogen atom, a lower acyl group, a lower alkoxy group, a lower alkoxycarbonyl group or a lower alkyl group; to thereby produce a half-sandwich organometallic ruthenium compound represented by the general formula (1).

Furthermore, the present invention provides a carbonylbis (diene)ruthenium complex characterized by being represented by the following general formula (7):

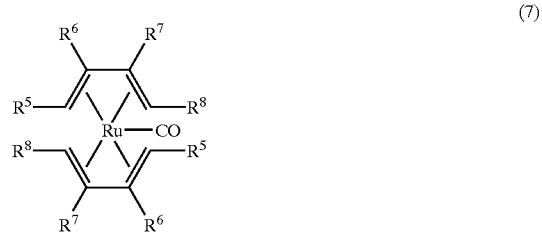
(7)

wherein $R^5$ to $R^8$ represent each hydrogen, an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and substituted alkyl group each has 1 to 6 carbon atoms, provided that the case where $R^5$ to $R^8$ are all hydrogen, and the case where $R^5$ and $R^8$ are hydrogen and $R^6$ and $R^7$ are methyl are excluded.

Furthermore, the present invention provides a process for producing the carbonylbis(diene)ruthenium complex as described above characterized in that a ruthenium chloride n-hydrate (wherein n is a number of 1 or more) is reacted with a diene in an alcohol in the presence of a zinc powder.

Furthermore, the present invention provides a process for producing a ruthenium-containing thin film characterized by using the carbonylbis(diene)ruthenium complex as described above as the precursor.

Figure 1:
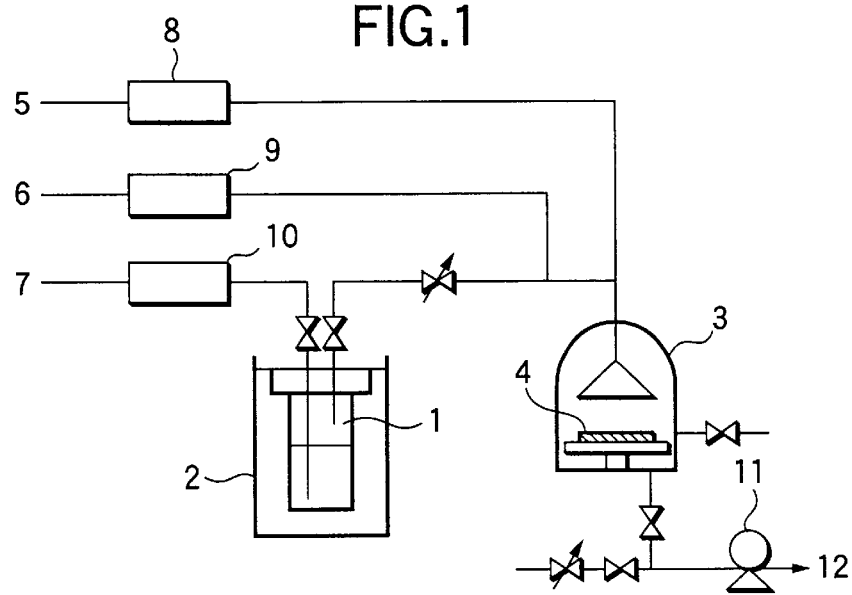
FIG. 1 is a diagram showing a schematic view of a CVD apparatus.

Description of Signs
1: precursor container
2: oil bath
3: reaction chamber
4: substrate
5: oxidation gas
6: counter gas
7: carrier gas
8: mass flow controller
9: mass flow controller
10: mass flow controller
11: vacuum pump
12: exhaust

DETAILED DESCRIPTION OF THE INVENTION

Now, the present invention will be illustrated in greater detail.

First, the definitions and specific examples of terms employed herein will be described.

Unless otherwise noted, the term "lower" as used herein means that the group having this term attached thereto is a linear, branched or cyclic hydrocarbyl group carrying from 1 to 6 carbon atoms.

Accordingly, examples of the lower alkyl group used in $R^1$, $R^2$, $R^3$ or $R^4$ include methyl group, ethyl group, n-propyl group, isopropyl group, n-butyl group, isobutyl group, sec-butyl group, tert-butyl group, pentyl (amyl) group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclopropyl group, cyclobutyl group, cyclopentyl group, cyclohexyl group, cyclopropylmethyl group, cyclopropylethyl group, cyclobutylmethyl group, etc. Preferable examples include methyl group, ethyl group, propyl group, isopropyl group and cyclopropyl group.

Specific examples of the lower alkoxy group used in $R^1$, $R^2$, $R^3$ or $R^4$ include methoxy group, ethoxy group, n-propoxy group, isopropoxy group, n-butoxy group, isobutoxy group, sec-butoxy group, tert-butoxy group, pentyloxy group, 1-methylbutyloxy group, 2-methylbutyloxy group, 3-methylbutyloxy group, 1,2-dimethylpropyloxy group, hexyloxy group, 1-methylpentyloxy group, 1-ethylpropyloxy group, 2-methylpentyloxy group, 3-methylpentyloxy group, 4-methylpentyloxy group, 1,2-dimethylbutyloxy group, 1,3-dimethylbutyloxy group, 2,3-dimethylbutyloxy group, 1,1-dimethylbutyloxy group, 2,2-dimethylbutyloxy group, 3,3-dimethylbutyloxy group, etc. Preferable examples include methoxy group, ethoxy group and propoxy group.

Examples of the lower alkoxycarbonyl group used in $R^1$, $R^2$, $R^3$ or $R^4$ include methoxycarbonyl group, ethoxycarbonyl group, propoxycarbonyl group, isopropoxycarbonyl group, cyclopropoxycarbonyl group, butoxycarbonyl group, isobutoxycarbonyl group, sec-butoxycarbonyl group, tert-butoxycarbonyl group, etc. Preferable examples include methoxycarbonyl group, ethoxycarbonyl group, propoxycarbonyl group, isopropoxycarbonyl group and cyclopropoxycarbonyl group.

Examples of the lower acyl group used in $R^1$, $R^2$, $R^3$ or $R^4$ include formyl group, acetyl group, propionyl group, butyryl group, isobutyryl group, valeryl group, 1-methylpropylcarbonyl group, isovaleryl group, pentylcarbonyl group, 1-methylbutylcarbonyl group, 2-methylbutylcarbonyl group, 3-methylbutylcarbonyl group, 1-ethylpropylcarbonyl group, 2-ethylpropylcarbonyl group, etc. Preferable examples include formyl group, acetyl group and propionyl group.

In $R^1$, $R^2$, $R^3$ or $R^4$, it is preferable to use, either the same or different, hydrogen or halogen atoms, in addition to the lower alkyl groups, lower alkoxy groups, lower alkoxycarbonyl groups and lower acyl groups as described above. Specific examples of the halogen atoms include fluorine, chlorine, bromine and iodine. Fluorine and chlorine are preferable.

The present invention relates to a half-sandwich organometallic ruthenium compound characterized by represented by the general formula (1) as described above. It preferably relates to a half-sandwich organometallic ruthenium compound characterized by being represented by the following general formula (2):

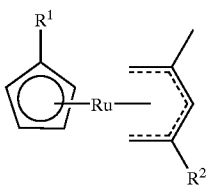
(2)

wherein $R^1$ and $R^2$ are the same or different and each represents hydrogen, a halogen atom, a lower acyl group, a lower alkoxy group, a lower alkoxycarbonyl group or a lower alkyl group, provided that the case where $R^1$ is hydrogen and $R^2$ is a methyl group is excluded. It is still preferable that $R^1$ and $R^2$ are both lower alkyl groups, in particular, $R^1$ is an ethyl group while $R^2$ is a methyl group.

Further, the present invention relates to a method of producing a ruthenium-containing thin film by the CVD method using the above-described half-sandwich organometallic ruthenium compound. FIG. 1 shows an example of an apparatus. A half-sandwich organometallic ruthenium compound according to the present invention is introduced into a precursor container 1 and maintained at 40 to 120° C. therein. Then a carrier gas 7 is bubbled into this liquid under reduced pressure so that the half-sandwich organometallic ruthenium compound is evaporated and transported to a reaction chamber 3. Then the half-sandwich organometallic ruthenium compound is heat-decomposed on a substrate 4 having been maintained at 200 to 750° C. by heating, thereby forming a ruthenium-containing thin film.

The CVD film-forming process according to the present invention may be carried out by the bubbling method as shown in FIG. 1. Alternatively, use may be made therefor of the solution vaporization method wherein the organometallic ruthenium compound according to the present invention per se or a solution thereof in an organic solvent is transported into a vaporization container and converted into a gas therein.

The half-sandwich organometallic ruthenium compound to be used in the CVD method according to the present invention may be used either as such or as a solution of the half-sandwich organometallic ruthenium compound dissolved in an organic solvent. Examples of the organic solvent usable herein include alcohols such as methanol, ethanol and isopropanol, esters such as ethyl acetate, butyl acetate and isoamyl acetate, glycol ethers such as ethylene glycol monoethyl ether, ethylene glycol monomethyl ether and ethylene glycol monobutyl ether, ethers such as diethyl ether, glyme, diglyme, triglyme and tetrahydrofuran, ketones such as methyl butyl ketone, methyl isobutyl ketone, ethyl butyl ketone, dipropyl ketone, diisobutyl ketone, methyl amyl ketone and cyclohexanone, and hydrocarbons such as hexane, cyclohexane, heptane, octane, benzene, toluene and xylene, though the invention is not restricted thereto.

A compound according to the present invention represented by the general formula (1) can be produced by reacting an open ruthenocene complex represented by the general formula (3) with a cyclopentadiene represented by the general formula (4). The open ruthenocene complex represented by the general formula (3) to be used therein can be obtained by reacting a pentadiene derivative represented by the general formula (5) with a halongenated ruthenium hydrate represented by the general formula (6) in the presence of zinc. The reaction formula (I) shows these reactions. In many of the conventional processes for producing these half-sandwich organometallic ruthenium compounds, a pentadiene derivative and a cyclopentadiene derivative are added at once and reacted and, as a result, only a poor yield can be established. In contrast thereto, the above-described production process makes it possible to obtain a target product at a high yield.

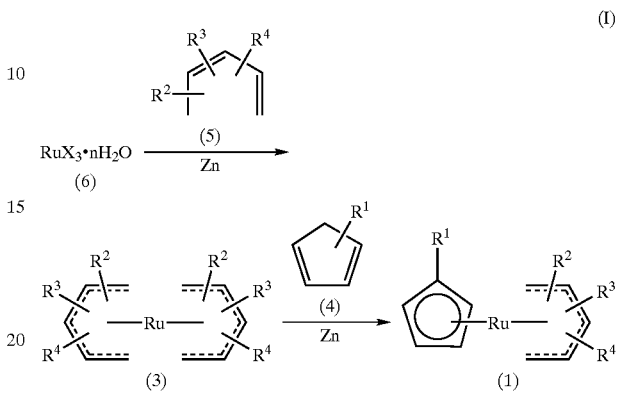
(I)

wherein X represents a halogen atom; n is a number of from 0 to 10; and $R^1$, $R^2$, $R^3$ and $R^4$ are each as defined above.

In this production process, the reaction solvent is not particularly restricted. Similarly, the procedures of collecting and purifying the product are not particularly restricted. However, the target product can be obtained via an industrially advantageous process by using methanol as the whole reaction solvent or a part thereof, filtering off the excessive zinc after the completion of the reaction, then extracting the half-sandwich organometallic ruthenium compound represented by the general formula (1) with the use of a solvent arbitrarily immiscible with methanol, concentrating and then distilling the thus obtained oily product. Examples of the solvent arbitrarily immiscible with methanol to be used therein include aliphatic hydrocarbons such as pentane, hexane, heptane and octane. Among all, pentane and hexane are particularly preferable, since they are economically available and industrially advantageous.

Although the amount of zinc to be used in the reaction according to the present invention is not particularly restricted, it is preferable to use 1.0 mol or more, still preferably 1.5 mol or more, of zinc per mol of the compound represented by the general formula (6) or the compound represented by the general formula (3). It is economically disadvantageous to use zinc in large excess. Namely, it is advantageous to use from 1.5 to 100 mol of zinc. In the step of reacting the compound represented by the general formula (5) with the compound represented by the general formula (6) in the presence of zinc, it is preferable to use 2 mol or excess of the compound represented by the general formula (5) per mol of the compound represented by the general formula (6). It is economically disadvantageous to use the compound in large excess. Namely, it is advantageous to use from 2 to 20 mol of the compound represented by the general formula (5).

In the step of reacting the compound represented by the general formula (5) with the compound represented by the general formula (6) in the presence of zinc, the reaction temperature preferably ranges from −20 to 100° C., still preferably from −20 to 80° C. In the step of reacting the compound represented by the general formula (3) with the compound represented by the general formula (4) in the presence of zinc, the reaction temperature preferably ranges from −20 to 100° C., still preferably from −20 to 80° C.

In the step of reacting the compound represented by the general formula (3) with the compound represented by the general formula (4) in the presence of zinc, it is preferable to use from 0.8 to 1.0 mol of the compound represented by the general formula (4) per mol of the compound represented by the general formula (3). In case where the compound represented by the general formula (4) is used in an amount less than 0.8 mol, a large amount of the compound represented by the general formula (3) remains unreacted. In case where the compound represented by the general formula (4) is used in an amount exceeding 1.0 mol, bis (ethylcyclopentadienyl)ruthenium is formed as a by-product in a large amount. Thus, both of these cases are unfavorable.

In case of producing the compound represented by the general formula (3) by reacting the compound represented by the general formula (5) with the compound represented by the general formula (6) in the present invention, it is preferable that the compound represented by the general formula (3) is not isolated but reacted as such in a single pot with the compound represented by the general formula (4) to thereby synthesize the compound represented by the general formula (1).

It is preferable that all of the reactions in the present invention are carried out in nitrogen gas or an noble gas atmosphere. Examples of the noble gas include helium, neon, argon, krypton, xenon and radon. Among these gases, nitrogen and argon are still preferable since they are economically available.

Next, the compound represented by the general formula (7) will be illustrated. Examples of such carbonylbis(diene) ruthenium complexes include carbonylbis(1,3-hexadiene) ruthenium [$R^5$ to $R^7$=—H, $R^8$=—$C_2H_5$], carbonylbis(2,4-hexadiene)ruthenium [$R^5$, $R^8$=—$CH_3$, $R^6$, $R^7$=—H], carbonylbis(3-methyl-1,3-pentadiene)ruthenium [$R^5$, $R^6$=—H , $R^7$, $R^8$=—$CH_3$], carbonylbis(2,4-hexadienal) ruthenium [$R^5$=—$CH_3$, $R^8$=—C=O, $R^6$, $R^7$=—H], carbonylbis(2,4-hexadien-1-ol)ruthenium [$R^5$=—$CH_3$, $R^8$=—$CH_2OH$, $R^6$, $R^7$=—H], carbonylbis(1-acetoxy-1,3-butadiene)ruthenium [$R^5$=—O—$COCH_3$, $R^6$, $R^7$, $R^8$=—H], carbonylbis(2,4-hexadienoic acid)ruthenium [$R^5$=—$CH_3$, $R^8$=—COOH, $R^6$, $R^7$=—H], carbonylbis(methyl 2,4-pentadienoate)ruthenium [$R^5$=—$COOCH_3$, $R^6$, $R^7$, $R^8$=—H], etc.

Further examples thereof include carbonylbis(2,4-heptadienal)ruthenium [$R^5$=—$C_2H_5$, $R^8$=—C=O, $R^6$, $R^7$=—H], carbonylbis(2,6-dimethyl-2,4,6-octatriene) ruthenium [$R^5$, $R^6$=—$CH_3$, $R^8$=—C=C($CH_3$)$_2$, $R^7$=—H], carbonylbis(ethyl 2,4-decadienoate)ruthenium [$R^5$=—$CH_2CH_2CH_2CH_2CH_3$, $R^8$=—$COOC_2H_5$, $R^6$, $R^7$=—H], carbonylbis(myrcene)ruthenium [$R^6$=—$CH_2CH_2CH$=C($CH_3$)$_2$, $R^5$, $R^7$, $R^8$=—H], carbonylbis(2,4-octadienal) ruthenium [$R^5$=—$CH_2CH_2CH_3$, $R^8$=—C=O, $R^6$, $R^7$=—H], carbonylbis(ethyl sorbate)ruthenium [$R^5$=—$CH_3$, $R^8$=—$COOC_2H_5$, $R^6$, $R^7$=—H], carbonylbis(methyl sorbate) ruthenium [$R^5$=—$CH_3$, $R^8$=—$COOCH_3$, $R^6$, $R^7$=—H], carbonylbis(2,4-heptadien-6-one)ruthenium [$R^5$=—$CH_3$, $R^8$=—$COCH_3$, $R^6$, $R^7$=—H], etc.

From the viewpoint of lowering the vaporization point of the complex, it is preferable that at least one of $R^5$ to $R^8$ is an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 or 2 carbon atoms while the remainder are hydrogen. It is still preferable that at least one of $R^5$ to $R^8$ is an alkyl group having 1 or 2 carbon atoms while the remainder are hydrogen. Among all, carbonylbis(2-methyl-1,3-pentadiene)ruthenium [$R^5$, $R^7$=—H, $R^6$, $R^8$=—$CH_3$] is the most desirable.

The carbonylbis(diene)ruthenium complex represented by the general formula (7) according to the present invention can be produced by reacting a ruthenium chloride n-hydrate with a diene in the presence of zinc in an alcohol. Shortage of the diene in this reaction results in the formation of metallic ruthenium and thus lowers the yield. It is therefore favorable to carry out the above reaction by using the diene in excess. Namely, it is preferable to use the diene in an amount 10 to 20 times by mol as much as the ruthenium chloride n-hydrate. To sufficiently reduce the ruthenium chloride n-hydrate, it is preferable to use the zinc powder in excess (10 times by mol or more) . In case of mixing these reactants, an alcoholic solution of the ruthenium chloride n-hydrate is dropped into the diene or an alcoholic solution of the diene having a zinc powder dispersed therein to thereby give the target carbonylbis(diene)ruthenium complex at a high yield.

The diene to be used herein is not particularly restricted, so long as it is a compound having 2 or more double bonds on a consecutive carbon chain in its molecule. Since double bonds transfer during the reaction, use may be made of an unconjugated diene such as 1,4-hexadiene, 1,5-hexadiene, 2-methyl-1,4-pentadiene, 3-methyl-1,4-pentadiene or 2-methyl-1,5-hexadiene. However, it is preferable to use a conjugated diene represented by the following general formula (8):

(8)

wherein $R^5$ to $R^8$ represent each hydrogen, an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 to 6 carbon atoms, provided that the case where $R^5$ to $R^8$ are all hydrogen, and the case where $R^5$ and $R^8$ are hydrogen and $R^6$ and $R^7$ are methyl are excluded.

In the general formula (8), it is preferable that at least one of $R^5$ to $R^8$ is an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 or 2 carbon atoms while the remainder are hydrogen.

Examples of such conjugated dienes include 1,3-hexadiene ($R^5$ to $R^7$=—H , $R^8$=—$C_2H_5$), 2,4-hexadiene ($R^5$, $R^8$=—$CH_3$, $R^6$, $R^7$=—H), 3-methyl-1,3-pentadiene ($R^5$, $R^6$=—H, $R^7$, $R^8$=—$CH_3$), 2,4-hexadienal ($R^5$=—$CH_3$, $R^8$=—C=O , $R^6$, $R^7$=—H), 2,4-hexadien-1-ol ($R^5$=—$CH_3$, $R^8$=—$CH_2OH$, $R^6$, $R^7$=—H), 1-acetoxy-1,3-butadiene ($R^5$=—O—$COCH_3$, $R^6$, $R^7$, $R^8$=—H), 2,4-hexadienoic acid ($R^5$=—$CH_3$, $R^8$=—COOH, $R^6$, $R^7$=—H), methyl 2,4-pentadienoate ($R^5$=—$COOHC_3$, $R^6$, $R^7$, $R^8$=—H) and 2,4-heptadienal ($R^5$=—$C_2H_5$, $R^8$=—C=O, $R^6$, $R^7$=—H).

Further examples thereof include 2,6-dimethyl-2,4,6-octatriene ($R^5$, $R^6$=—$CH_3$, $R^8$=—C=C($CH_3$)$_2$, $R^7$=—H) , ethyl 2,4-decadienoate ($R^5$=—$CH_2CH_2CH_2CH_2CH_3$, $R^8$=—$COOC_2H_5$, $R^6$, $R^7$=—H), myrcene ($R^6$=—$CH_2CH_2CH$=C($CH_3$)$_2$, $R^5$, $R^7$, $R^8$=—H) 2,4-octadienal ($R^5$=—$CH_2CH_2CH_3$, $R^8$=—C=O, $R^6$, $R^7$=—H), ethyl sorbate ($R^5$=—$CH_3$, $R^8$=—$COOC_2H_5$, $R^6$, $R^7$=—H), methyl sorbate ($R^5$=—$CH_3$, $R^8$=—$COOCH_3$, $R^6$, $R^7$=—H), 2,4-heptadien-6-one ($R^5$=—$CH_3$, $R^8$=—$COCH_3$, $R^6$, $R^7$=—H), etc. Among all, 2-methyl-1,3-pentadiene ($R^5$, $R^7$=—H, $R^6$, $R^8$=—$CH_3$) is the most desirable.

The alcohol is not particularly restricted, so long as it is in the state of a liquid at room temperature (25° C). Since CO serving as a ligand is formed from the alcohol, it is preferable to use methanol, ethanol or 1-propanol from the viewpoint of reaction rate. Either a single alcohol or a mixture of several alcohols may be used. In case of dropping an alcoholic solution of the ruthenium chloride n-hydrate into the diene or an alcoholic solution of the diene containing the zinc powder dispersed therein, the alcohol to be used for the dissolution of the diene and the alcohol to be used for the dissolution of the ruthenium chloride n-hydrate may be either the same or different. The reaction proceeds slowly at a low temperature while the polymerization of the diene arises at a high temperature. Accordingly, it is preferable that the reaction temperature ranges from 0 to 80° C. After the completion of the reaction, the zinc powder is filtered off. Then the complex thus formed may be extracted with a solvent such as pentane or hexane either directly from the reaction mixture or after removing the alcohol and the unreacted diene therefrom. Since the thus extracted complex is contaminated with diene polymers and the like formed during the reaction, it is purified by chromatography, distillation, etc.

Using these carbonylbis(diene)ruthenium complexes as a precursor, ruthenium-containing thin films can be produced.

In case of producing a thin film containing ruthenium such as ruthenium or ruthenium oxide on a substrate by the CVD method with the use of a carbonylbis(diene)ruthenium complex as the precursor, the carbonylbis(diene)ruthenium complex is vaporized and supplied onto the substrate. Examples of the vaporization method include a method wherein an inert carrier gas is introduced into the heated complex in the state of a liquid and then the complex is supplied in association with the carrier gas into a reaction chamber having the substrate placed therein; a method wherein the complex is dissolved in an organic solvent to give a solution, then the solution is supplied into a vaporizer in which it is vaporized and the gas is supplied into a reaction chamber having a substrate placed therein; etc.

In case where the carbonylbis(diene)ruthenium complex is used in the form of a solution in an organic solvent, examples of the organic solvent include alcohols such as methanol, ethanol and isopropanol, esters such as ethyl acetate, butyl acetate and isoamyl acetate, glycol ethers such as ethylene glycol monoethyl ether, ethylene glycol monomethyl ether and ethylene glycol monobutyl ether, ethers such as glyme, diglyme, triglyme and tetrahydrofuran, ketones such as methyl butyl ketone, methyl isobutyl ketone, ethyl butyl ketone, dipropyl ketone, diisobutyl ketone, methyl amyl ketone and cyclohexanone, and hydrocarbons such as hexane, cyclohexane, heptane, octane, toluene and xylene, though the invention is not restricted thereto.

To form a thin film containing ruthenium such as ruthenium or ruthenium oxide on a substrate by the coating heat decomposition method, the carbonylbis(diene)ruthenium complex is also used in the form of a solution. In this case, use can be also made of the above-described organic solvents.

The CVD method to be used in producing the ruthenium-containing thin film according to the present invention is not particularly restricted, so long as it is a CVD method commonly employed in the art, for example, thermal CVD, plasma CVD or photo-CVD. In the coating heat decomposition method, the precursor may be coated by, for example, the spin coating method, the dipping method or the spraying method. For heating, use can be made of an oven, a hot plate or the like. The coating method, the heating method and the combination thereof are not particularly restricted.

The half-sandwich organometallic ruthenium compound represented by the general formula (1) according to the present invention is in the state of liquid at room temperature and has a sufficient vapor pressure at around 100° C. Owing to these characteristics, it can be quantitatively supplied as a CVD precursor by gas bubbling. Compared with the conventional precursors, it can be heat-decomposed at a low temperature. Thus a ruthenium-containing thin film having excellent step coverage can be formed thereby on a substrate. According to the present invention, a ruthenium-containing thin film can be produced by the CVD method which is excellent in mass productivity.

By the CVD method with the use of the organometallic ruthenium compound according to the present invention, either an Ru film or an $RuO_2$ film can be formed by controlling the oxygen flow rate. The ruthenium-containing thin film thus obtained has a high density, is contaminated with little impurities and shows an excellent crystallinity. As a result, it is possible to obtain an ruthenium-containing thin film having a favorable resistivity close to the bulk level. Compared with thin films obtained by using the conventional products, the ruthenium-containing thin film according to the present invention has a high density and a flat thin film surface.

According to the process for producing a half-sandwich organometallic ruthenium compound of the present invention, the half-sandwich organometallic ruthenium compound, which can be obtained only at a low yield by the conventional methods, can be stably obtained at a high yield. Moreover, the target product can be obtained by this process without concentrating an alcohol, which brings about a merit from the viewpoint of energy consumption. Accordingly, the process for producing a half-sandwich organometallic ruthenium compound of the present invention is widely applicable not only to small-scaled production of these products but also production thereof on an industrial scale.

Using the carbonylbis(diene)ruthenium complex according to the present invention, a film can be formed at a low temperature compared with the complexes which have hitherto been employed in the film-formation by the CVD method, and, moreover, a ruthenium-containing thin film can be formed while supplying the precursor in a stable state. In addition, the carbonylbis(diene)ruthenium complex has a low heat decomposition temperature and a high solubility in solvents, which makes it usable in the formation of an ruthenium-containing thin film by the coating heat decomposition method too. It is further expected as being usable as a reaction catalyst in a solvent. Compared with the conventionally known process for producing a carbonylbis(diene)ruthenium complex, it can be produced under mild conditions and, therefore, advantageous in production.

Now, the present invention will be described in greater detail by reference to the following Examples. However, it is to be understood that the present invention is not construed as being restricted thereto.

EXAMPLE 1

Synthesis of (2,4-dimethylpentadienyl)(ethylcyclopentadienyl)ruthenium and Heat Decomposition Properties Thereof 400 g of zinc was weighed into a four-necked flask. After purging the container with argon, 205 ml of 2,4-dimethyl- 1,3-pentadiene was added thereto to give a suspension. Then a solution of 30 g of ruthenium trichloride n-hydrate (n: about 3) dissolved in 1000 ml of methanol was dropped thereinto at room temperature over 40 minutes. After the completion of the dropping, the mixture was stirred at room temperature for 30 minutes, then heated to 60° C. and stirred for additional 2 hours. The mixture was once cooled by allowing to stand and then 12 ml of ethylcyclopentadiene was added thereto. The resultant mixture was stirred as such at room temperature for 30 minutes, then heated to 60° C. and stirred for additional 2 hours. After the completion of the reaction, the mixture was cooled to room temperature and the unreacted zinc was removed with the use of a glass filter. Next, it was extracted with hexane (750 ml×1,300 ml×4). The extracts were concentrated under reduced pressure and the oily product thus obtained was distilled under reduced pressure to thereby give 25.4 g of target (2,4-dimethylpentadienyl) (ethylcyclopentadienyl)ruthenium (yield: 76.3%).

Oily yellow product:

$^1$H-NMR (500 MHz, CDCl$_3$, δ ppm) 5.38 (s, 1H), 4.63 (t, J=2.0 Hz, 2H), 4.52(t, J=2.0 Hz, 2H), 2.70 (d, J=2.5 Hz, 2H), 2.15 (q, J=7.5 Hz, 2H), 1.93 (s, 6H), 1.12 (t, J=7.5 Hz, 3H), −0.09 (d, J=2.5 Hz, 2H)

IR (neat, cm$^{-1}$)

3050, 2960, 2910, 1475, 1445, 1430, 1375, 1030, 860, 800

MS (GC/MS, EI)

Figure 2:
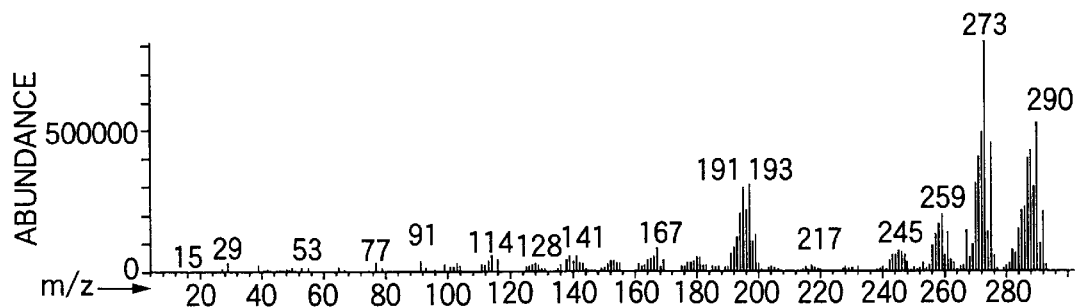
FIG. 2 shows an MS chart of the measurement in Example 1.

A molecular ion peak of (2,4-dimethylpentadienyl) (ethylcyclopentadienyl)ruthenium at $^{102}$Ru:m/z 290. FIG. 2 shows this MS chart.

(Decomposition Properties)

Figure 3:
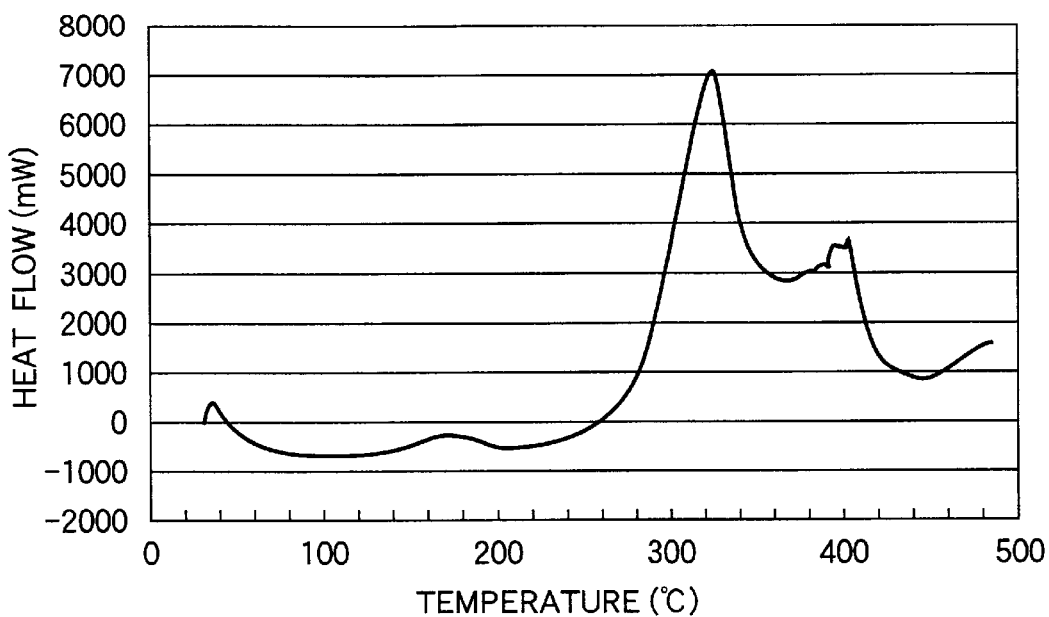
FIG. 3 is a graph showing the results of decomposition properties (DSC) measured in Example 1.

FIG. 3 shows the results of the measurement of the decomposition properties of the (2,4-dimethylpentadienyl) (ethylcyclopentadienyl)ruthenium thus obtained. The decomposition properties were measured under the following conditions.

Measurement method:

power compensation differential scanning calorimetry (DSC)

Measurement conditions:

reference: alumina inert gas: nitrogen 50 ml/min heating rate: 10° C./min

Comparative Example 1

Decomposition Properties of bis (ethylcyclopentadienyl)ruthenium

Figure 4:
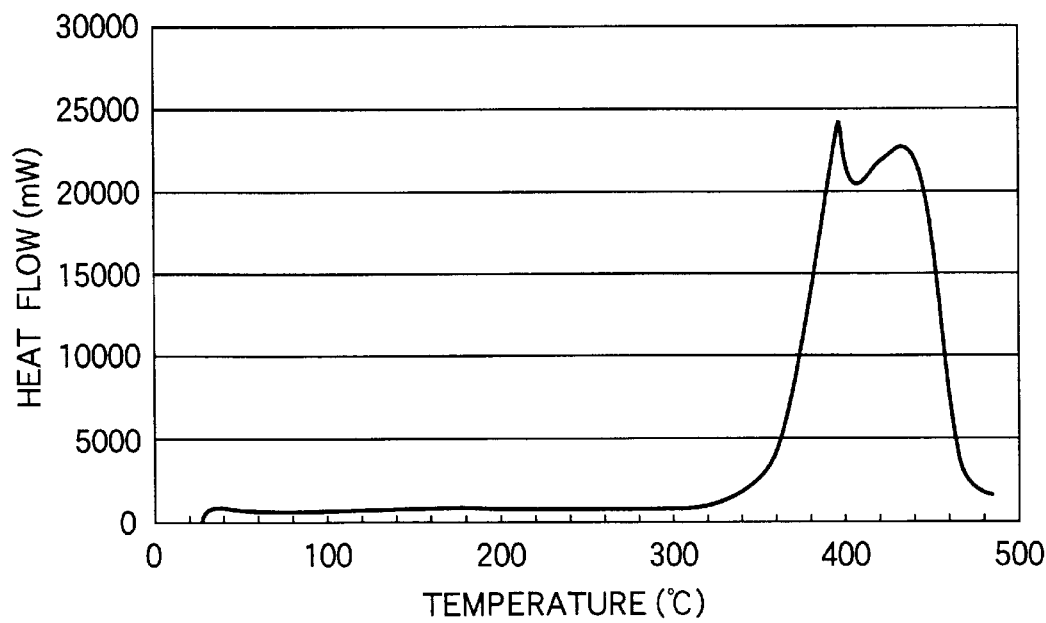
FIG. 4 is a graph showing the results of decomposition properties (DSC) measured in Comparative Example 1.

The decomposition properties of bis(ethylcyclopentadienyl)ruthenium were measured under the same conditions as in Example 1. An exothermic reaction was observed from about 320° C. FIG. 4 shows the results.

EXAMPLE 2

Synthesis of (2,4-dimethylpentadienyl) (methylcyclopentadienyl)ruthenium 8.0 g of zinc was weighed into a 50 ml Schlenk tube. After purging the container with argon, 4 ml of 2,4-dimethyl-1, 3-pentadiene was added thereto to give a suspension. Then a solution of 0.6 g of ruthenium trichloride hydrate dissolved in 20 ml of ethanol was dropped thereinto at room temperature over 50 minutes. After the completion of the dropping, the mixture was stirred at room temperature for 30 minutes, then heated to 70° C. and stirred for additional 2 hours. The mixture was once cooled by allowing to stand and then 240 µl of methylcyclopentadiene was added thereto. The resultant mixture was stirred as such at room temperature for 30 minutes, then heated to 70° C. and stirred for additional 2 hours. After the completion. of the reaction, the mixture was cooled to room temperature and the unreacted zinc was removed with the use of a glass filter. Next, it was concentrated to give a pasty mixture. The obtained pasty mixture was extracted with pentane and the extract was subjected to column chromatography with the use of alumina as a carrier and pentane as an eluent. Thus, 0.28 g of target (2,4-dimethylpentadienyl)(methylcyclopentadienyl)ruthenium was obtained.

$^1$H-NMR (500 MHz, CDCl$_3$, δ ppm) 5.36 (s, 1H), 4.61 (t, J=2.0 Hz, 2H), 4.57(t, J=2.0 Hz, 2H), 2.67 (d, J=2.5 Hz, 2H), 1.93 (s, 6H), 1.83 (s, 3H), −0.07 (d, J=2.5 Hz, 2H)

MS (GC/MS, EI)

Figure 5:
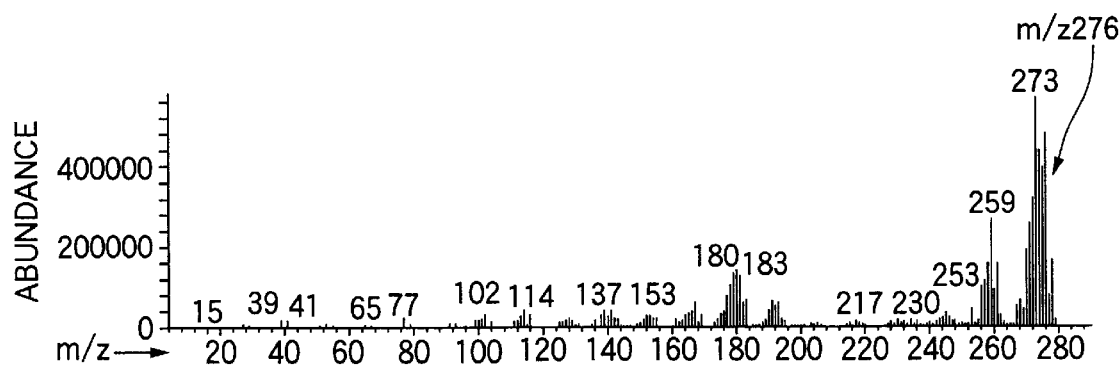
FIG. 5 shows an MS chart of the measurement in Example 2.

A molecular ion peak of (2,4-dimethylpentadienyl) (methylcyclopentadienyl)ruthenium at $^{102}$Ru:m/z 276. FIG. 5 shows this MS chart.

EXAMPLE 3

Production of Ruthenium-containing Thin Film by the CVD Method Using (2,4-dimethylpentadienyl) (ethylcyclopentadienyl)ruthenium as Precursor Using an apparatus shown in FIG. 1, an Si substrate having an SiO$_2$ film (100 nm) formed on its surface was employed as the substrate. About 10 g of (2,4-dimethylpentadienyl)(ethylcyclopentadienyl)ruthenium was fed into a precursor container 1 and heated in an oil bath to achieve a thermostatic state at 60° C. A reaction chamber 3 and the inside of a precursor container 1 were controlled respectively to 10 Torr and 100 Torr with the use of a vacuum pump 11 and a pressure-controlling valve. Nitrogen was employed as a carrier gas 7 and its flow rate was set to 100 sccm by using a mass flow controller. Oxygen was employed as an oxidation gas 5 while nitrogen was employed as a counter gas 6. The flow rate of the oxidation gas was set to 0, 10, 30 and 300 sccm while the flow rate of the counter gas was set to such levels as giving the sum with the oxidation gas of 500 sccm respectively. The temperature of substrate 4 was set to 400° C. and film-formation was performed for 60 minutes under heating.

Figure 6:
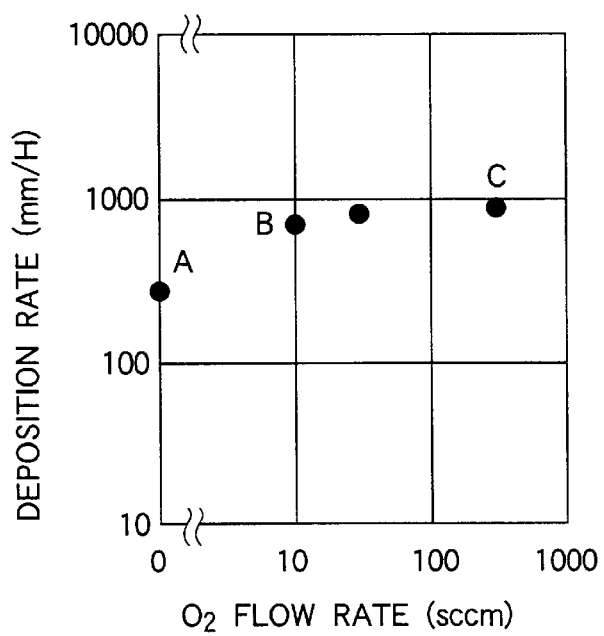
FIG. 6 is a graph showing the relationship between oxygen flow rate and deposition rate in Example 3.
Figure 7:
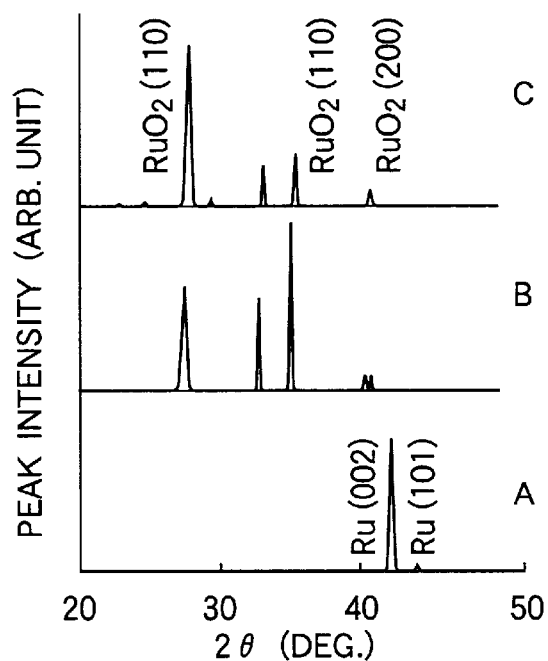
FIG. 7 is a chart showing the X-ray diffractometry pattern of the film produced in Example 3.

FIG. 6 shows the film thickness of the ruthenium-containing thin film formed on the substrate vs. oxygen flow rate. FIG. 7 shows the X-ray diffraction patterns of the films obtained in A, B and C in FIG. 6. As FIG. 7 clearly shows, an Ru film was obtained at the oxygen flow rate of 0 sccm (A), while RuO$_2$ films were obtained at the oxygen flow rate of larger than 0 sccm (B) or (C). Namely, it has been found out that either an Ru film or an RuO$_2$ film can be produced by controlling the oxygen flow rate in the CVD.

EXAMPLE 4

Production of Ruthenium-containing Thin Film by the CVD Method Using (2,4-dimethylpentadienyl) (ethylcyclopentadienyl)ruthenium as Precursor Using an apparatus shown in FIG. 1, an Si substrate having an SiO$_2$ film (100 nm) formed on its surface was employed as the substrate. About 10 g of (2,4-dimethylpentadienyl)(ethylcyclopentadienyl)ruthenium was fed into a precursor container 1 and heated in an oil bath to achieve a thermostatic state at 60° C. A reaction chamber 3 and the inside of a precursor container were controlled respectively to 10 Torr and 100 Torr with the use of a vacuum pump 11 and a pressure-controlling valve. Nitrogen was employed as a carrier gas 7 and its flow rate was set to 100 sccm by using a mass flow controller. Oxygen was employed as an oxidation gas 5 while nitrogen was employed as a counter gas 6. The flow rate of the oxidation gas was set to 300 sccm while the flow rate of the counter gas was set to 200 sccm. The temperature of substrate 4 was set to 170, 200, 300, 400, 500 and 600° C. and film-formation was performed for 60 minutes under heating to each temperature.

Figure 8:
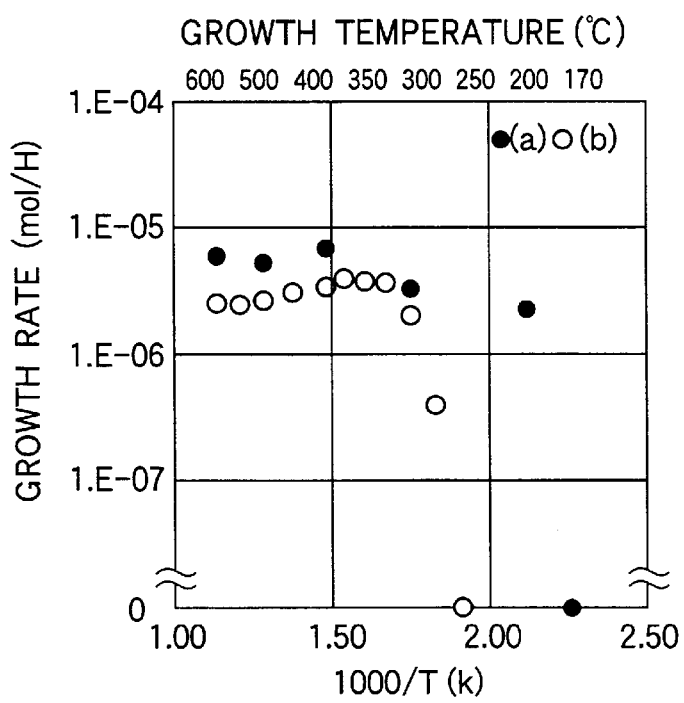
FIG. 8 is a graph showing the Arrehenius plot of the film growth rate.
Figure 9:
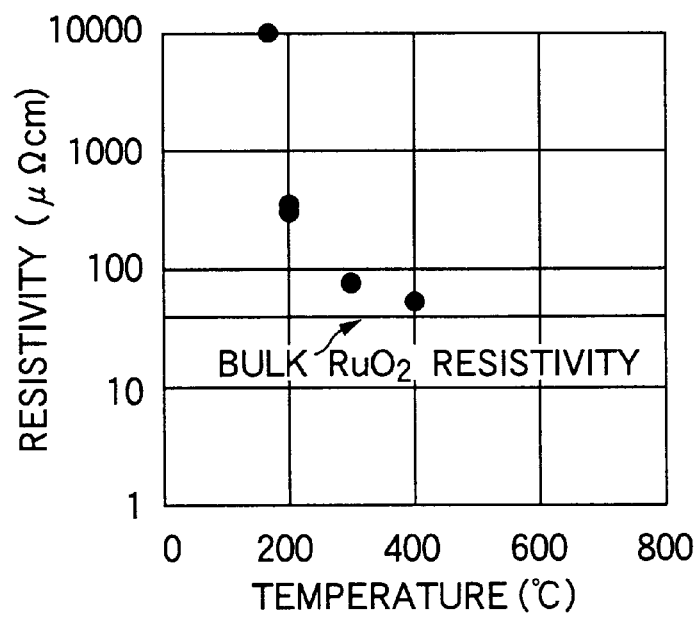
FIG. 9 is a graph showing the resistivities of the films obtained in Example 4.

The close circles (a) in FIG. 8 show the Arrehenius plot of the film growth rate. Ruthenium-containing thin films could be formed at 200 ° C. and higher. FIG. 9 shows the resistivities of the obtained films. Favorable resistivities close to the bulk resistivity (indicated by the arrow in FIG. 9) were obtained.

EXAMPLE 5

Production of Ruthenium-containing Thin Film by the CVD Method Using (2,4-dimethylpentadienyl)(ethylcyclopentadienyl)ruthenium as Precursor Using an apparatus shown in FIG. 1, an Si substrate having an $SiO_2$ film (100 nm) formed on its surface was employed as the substrate. About 10 g of (2,4-dimethylpentadienyl)(ethylcyclopentadienyl)ruthenium was fed into a precursor container 1 and heated in an oil bath to achieve a thermostatic state at 60° C. A reaction chamber 3 and the inside of a precursor container were controlled respectively to 10 Torr and 100 Torr with the use of a vacuum pump 11 and a pressure-controlling valve. Nitrogen was employed as a carrier gas 7 and its flow rate was set to 100 sccm by using a mass flow controller. Without using any oxidation gas, nitrogen was employed as a counter gas 6 and the flow rate of the counter gas was set to 500 sccm. The temperature of substrate 4 was set to 250, 275, 300, 325, 350, 375, 400, 450, 500, 550 and 600° C. and film-formation was performed for 60 minutes under heating to each temperature.

Figure 10:
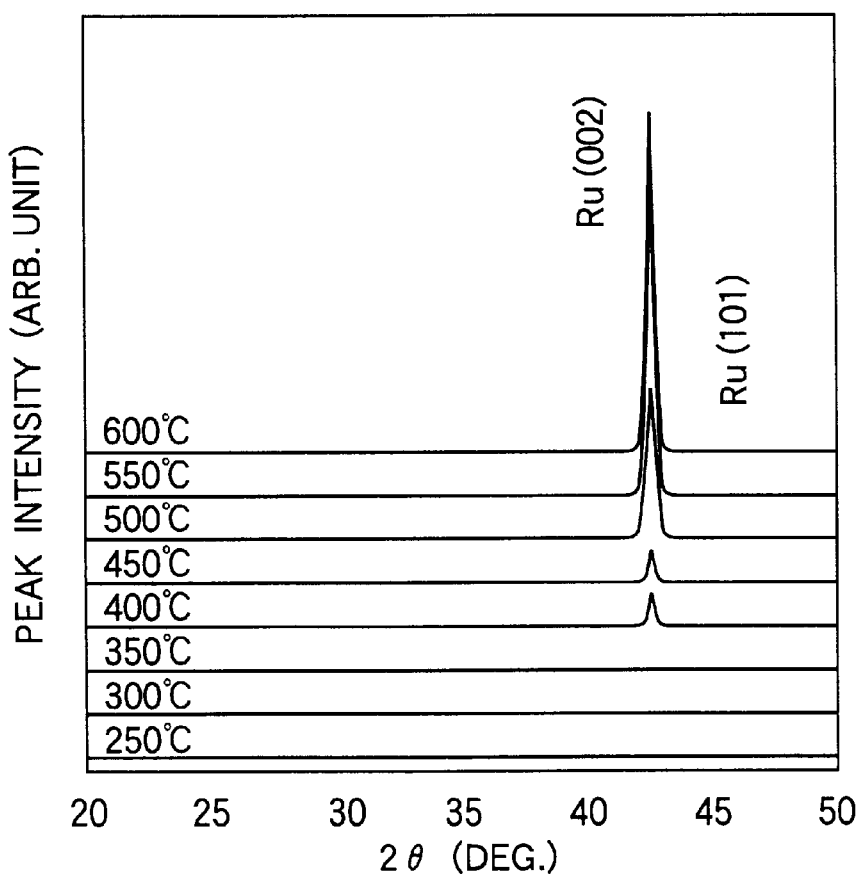
FIG. 10 is a chart showing the X-ray diffractometry pattern of the film obtained in Example 5.
Figure 11:
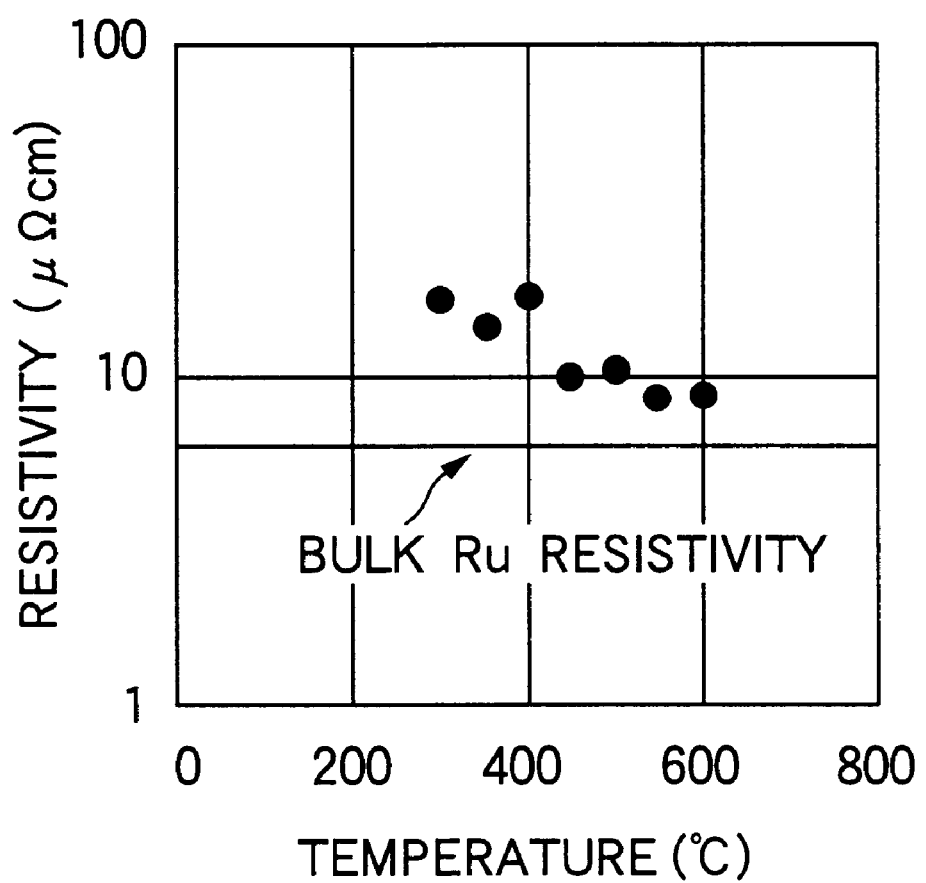
FIG. 11 is a graph showing the resistivities of the films obtained in Example 5.
Figure 12:
FIG. 12 is an SEM photograph of the film obtained in Example 5.
Figure 14:
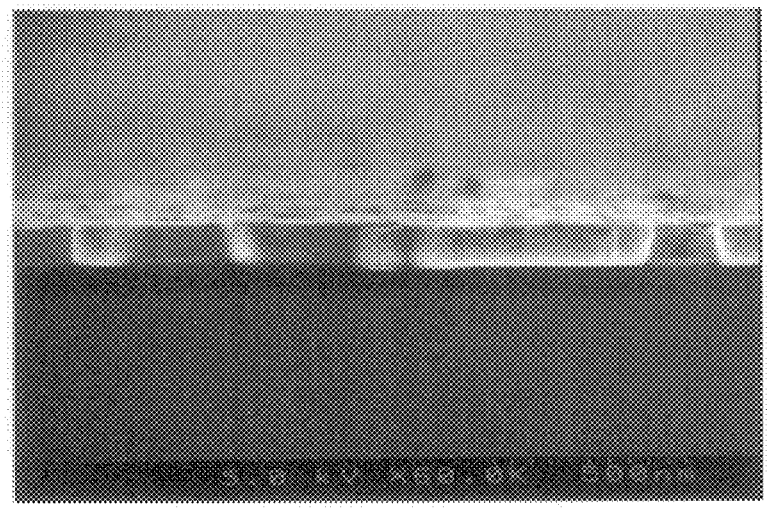
FIG. 14 is an SEM photograph of the film obtained in Example 5.
Figure 16:
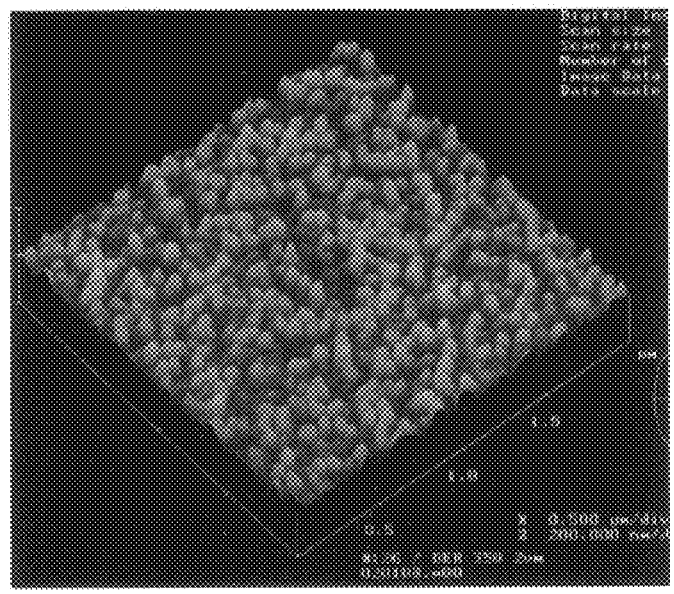
FIG. 16 is an AFM photograph of the film obtained in Example 5.
Figure 18:
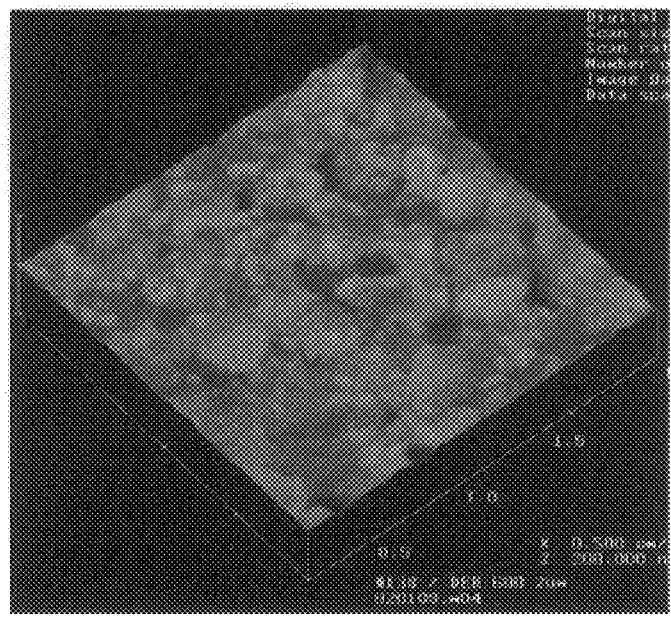
FIG. 18 is an AFM photograph of the film obtained in Example 5.

The open circles (b) in FIG. 8 show the Arrehenius plot of the film growth rate. Ruthenium-containing thin films could be formed at 275° C. and higher. FIG. 10 shows the X-ray diffraction patterns of the ruthenium-containing thin films thus formed. Films with favorable crystallinity were obtained at 400° C. and higher. FIG. 11 shows the resistivities of the obtained films. Favorable resistivities close to the bulk resistivity (indicated by the arrow in FIG. 11) were obtained. FIGS. 12 and 14 show the SEM photographs of the cross-sections of the films formed at substrate temperatures of 300° C. and 600° C. respectively. Although a dense film was observed at each temperature, the film formed at 600° C. was superior in density. FIGS. 16 and 18 show the AFM images of the sections of the films formed at substrate temperatures of 350° C. and 600° C. respectively. Table 1, (a) shows Ra (arithmetic mean roughness) and Ry (maximum height) obtained as the results of the measurement of surface roughness by AFM. Ra and Ry were determined in accordance with the methods described in JIS B0601-1994 and JIS B0031-1994 respectively. Thus, it can be understood that each ruthenium-containing thin films of the present invention has an extremely flat surface.

TABLE 1

| Substrate temp. | (a) Example 6 | | (b) Comp. Example 2 | |
|---|---|---|---|---|
| (° C.) | Ra | Ry | Ra | Ry |
| 300 | 4.75 | 61.12 | 20.07 | 223.26 |
| 600 | 4.14 | 72.25 | 26.23 | 326.45 |

Comparative Example 2

Figure 13:
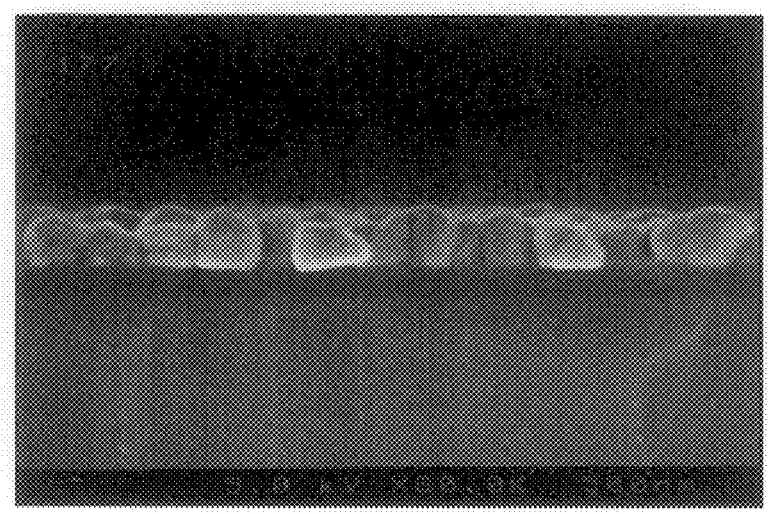
FIG. 13 is an SEM photograph of the film obtained in Comparative Example 2.
Figure 15:
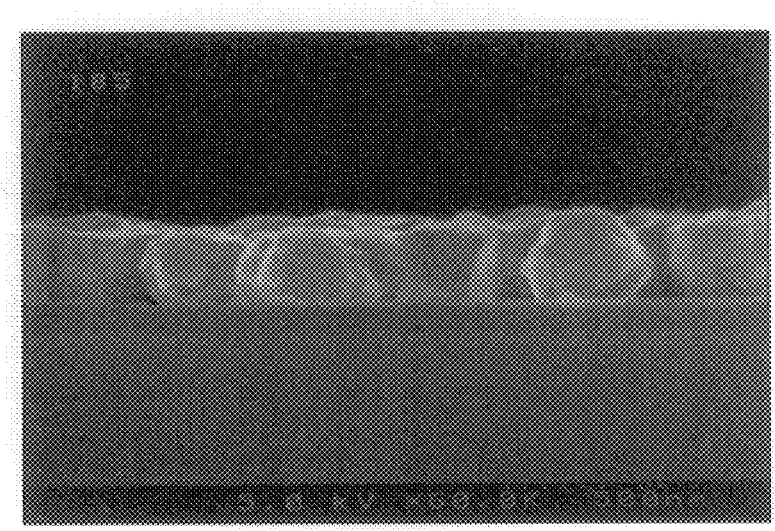
FIG. 15 is an SEM photograph of the film obtained in Comparative Example 2.
Figure 17:
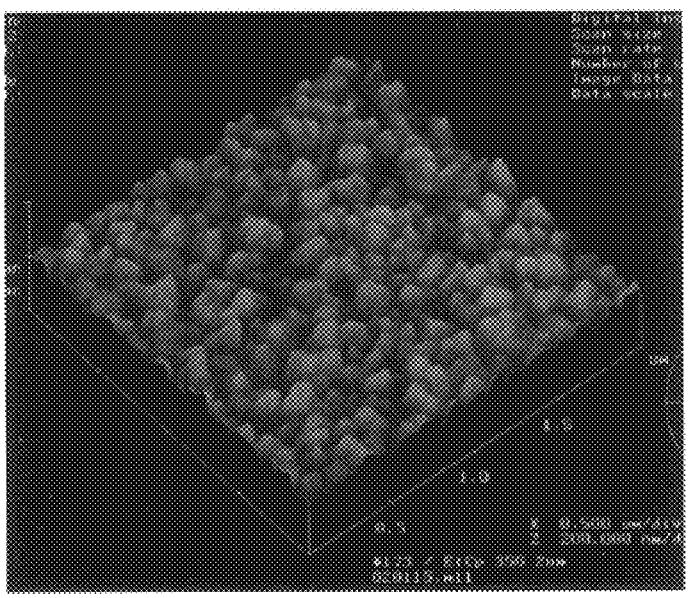
FIG. 17 is an AFM photograph of the film obtained in Comparative Example 2.
Figure 19:
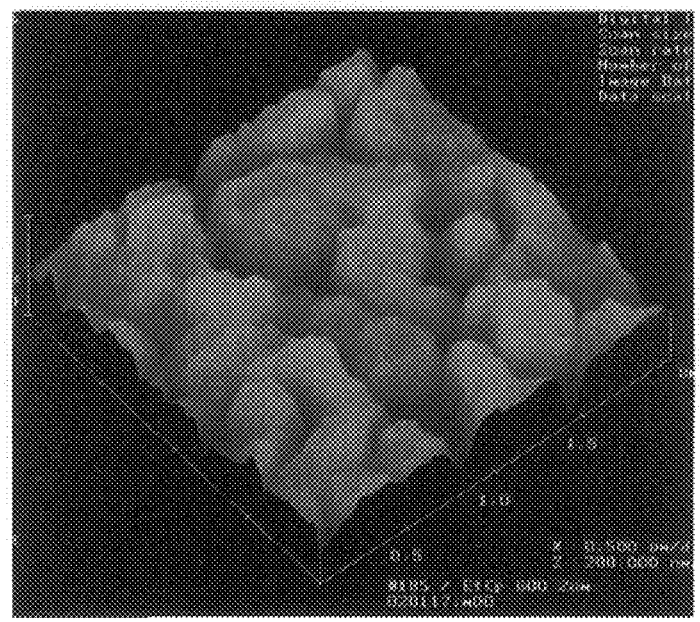
FIG. 19 is an AFM photograph of the film obtained in Comparative Example 2.

Film-formation was carried out by using an apparatus shown in FIG. 1 as in Example 5 but supplying about 10 g of marketed bis(ethylcyclopentadienyl)ruthenium to the precursor container 1. FIGS. 13 and 15 show the SEM photographs of the cross-sections of the films formed at substrate temperatures of 300° C. and 600° C. respectively. In each case, the film was poor in density and the growth of column crystals was observed.. FIGS. 17 and 19 show the AFM images of the sections of the films formed at substrate temperatures of 350° C. and 600° C. respectively. Table 1, (b) shows Ra and Ry obtained as the results of the measurement of surface roughness by AFM. Compared with the above Example, large surface roughness was observed.

EXAMPLE 6

Figure 20:
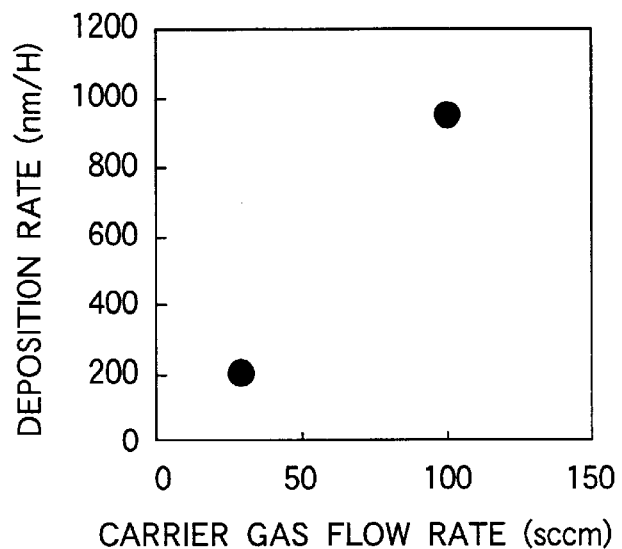
FIG. 20 is a graph showing the relationship between carrier gas flow rate and deposition rate in Example 6.

Production of Ruthenium-containing Thin Film by the CVD Method Using (2,4-dimethylpentadienyl)(ethylcyclopentadienyl)ruthenium as Precursor Using an apparatus shown in FIG. 1, an Si substrate having an $SiO_2$ film (100 nm) formed on its surface was employed as the substrate. About 10 g of (2,4-dimethylpentadienyl)(ethylcyclopentadienyl)ruthenium was fed into a precursor container 1 and heated in an oil bath to achieve a thermostatic state at 60° C. A reaction chamber 3 and the inside of a precursor container were controlled respectively to 10 Torr and 100 Torr with the use of a vacuum pump 11 and a pressure-controlling valve. Nitrogen was employed as a carrier gas 7 and its flow rate was set to 30 and 100 sccm by using a mass flow controller. Oxygen was employed as an oxidation gas 5 while nitrogen was employed as a counter gas 6. The flow rate of the oxidation gas was set to 300 sccm while the flow rate of the counter gas was set to 200 sccm. The temperature of substrate 4 was set to 400° C. and film-formation was performed for 60 minutes under heating. FIG. 20 shows the relationship between carrier gas flow rate and deposition rate of the ruthenium-containing thin film formed on the substrate. A film could be sufficiently formed even in the region with the use of a small amount of the carrier gas.

EXAMPLE 7

Production of Ruthenium-containing Thin Film by the CVD Method Using (2,4-dimethylpentadienyl)(ethylcyclopentadienyl)ruthenium as Precursor Using an apparatus shown in FIG. 1, an Si substrate having an $SiO_2$ film (100 nm) formed on its surface was employed as the substrate. About 10 g of (2,4-dimethylpentadienyl)(ethylcyclopentadienyl)ruthenium was fed into a precursor container 1 and heated in an oil bath to achieve a thermostatic state at 60° C. A reaction chamber 3 and the inside of a precursor container were controlled respectively to 10 Torr and 100 Torr with the use of a vacuum pump 11 and a pressure-controlling valve. Nitrogen was employed as a carrier gas 7 and its flow rate was set to 100 sccm by using a mass flow controller. Without using any oxidation gas 5, nitrogen was employed as a counter gas 6. The flow rate of the counter gas was set to 500 sccm. The temperature of substrate 4 was set to 350° C. and film-formation was performed for 2.5, 5, 10, 20, 60 and 120 minutes under heating.

Figure 21:
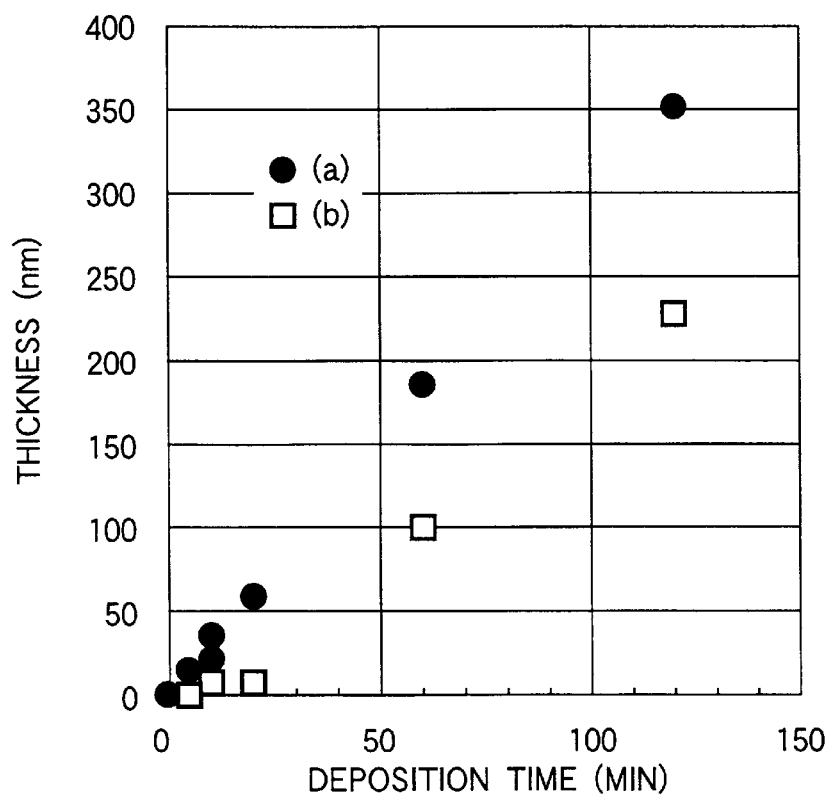
FIG. 21 is a graph showing the relationship between deposition time and film thickness.

The close circles (a) in FIG. 21 show each the deposition time and the film thickness of the ruthenium-containing thin film formed on the substrate. Ruthenium-containing thin films were obtained at deposition time of 2.5 minutes and longer and the film thickness was increased linearly as the deposition time was prolonged. The ruthenium-containing thin film according to the present invention can be easily formed without showing any incubation time (the time wherein no film is formed on the substrate).

Comparative Example 3

Film-formation was carried out by using an apparatus shown in FIG. 1 as in Example 7 but supplying about 10 g of marketed bis(ethylcyclopentadienyl)ruthenium to the precursor container 1. The squares (b) in FIG. 21 show each the deposition time and the film thickness of the ruthenium-containing thin film formed on the substrate. An incubation time was observed until the deposition time attained 20 minutes.

EXAMPLE 8

Synthesis of carbonylbis(2-methyl-1,3-pentadiene) ruthenium 160 g of a zinc powder was introduced into a 1000 ml four-necked flask. After attaching a stirrer, a dropping funnel, a condenser and a thermometer, the flask was purged with argon. Then, 60 ml of 2-methyl-1,3-pentadiene was added and the zinc powder was dispersed therein by stirring. Next, 10 g of ruthenium chloride n-hydrate dissolved in 400 ml of ethanol was dropped thereinto over 1 hour from the dropping funnel while maintaining the temperature at 25° C. or below in a water bath. After the completion of the dropping, the resultant mixture was heated to 70° C. and stirred for 3 hours. The zinc powder was filtered off from the reaction mixture and ethanol, etc. were removed under reduced pressure. The pasty product thus obtained was extracted with pentane. The extract was purified by column chromatography with the use of alumina as a packing and pentane as a solvent. After removing the solvent, 9.99 g of carbonylbis(2-methyl-1,3-pentadiene)ruthenium was obtained as a yellow liquid (yield: 89%).

$^1$H-NMR (CDCl$_3$) δ3.91 (d, 2H, J=7.5 Hz), 2.04 (s, 6H), 1.42 (s, 2H), 1.27 (d, 6H, J=6 Hz), 1.17 (dq, 2H, J=14 Hz), 0.30 (s, 2H)

$^{13}$C-NMR (CDCl$_3$) δ218.88 (CO), 91.51 (C), 89.47 (CH), 50.51 (CH), 37.58 (CH$_2$), 22.84 (CH$_3$), 18.78 (CH$_3$)

IR 1967 cm$^{-1}$ (CO)

MS 294 (M$^+$)

EXAMPLE 9

Figure 22:
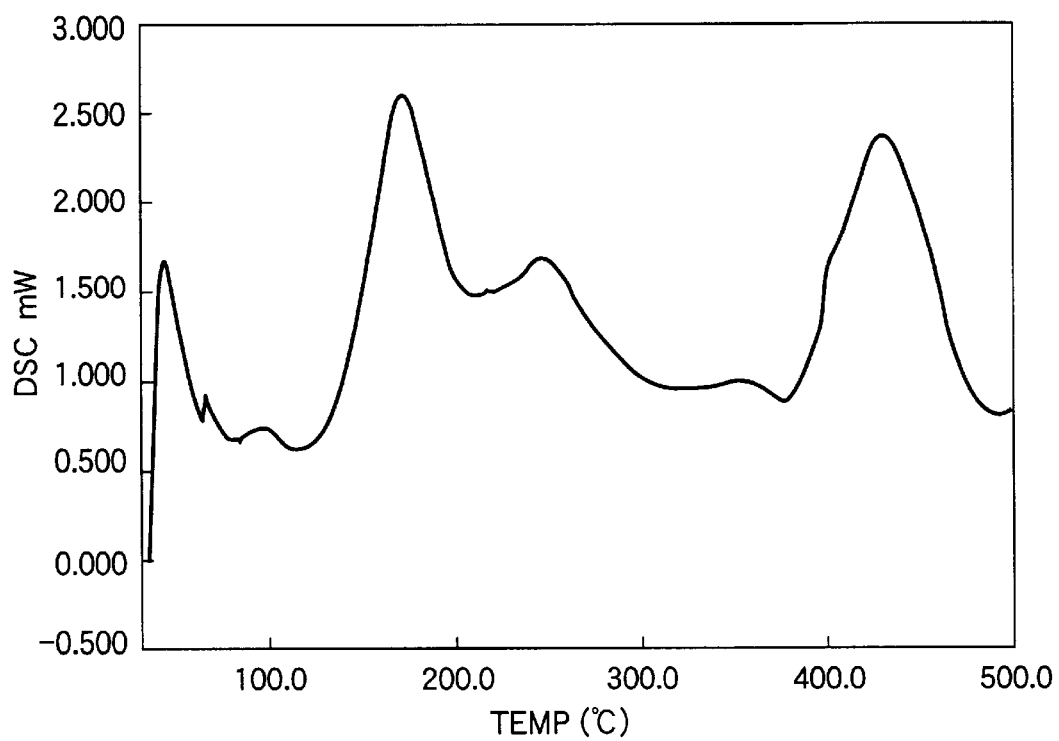
FIG. 22 is a graph showing the DSC curve of Example 9.

Heat Decomposition Properties (Measured by DSC) of carbonylbis(2-methyl-1,3-pentadiene)ruthenium 6.7 mg of the carbonylbis(2-methyl-1,3-pentadiene) ruthenium obtained in Example 8 was introduced into a stainless pan and air-tightly covered with a stainless lid. This sample was heated at a rate of 10° C./min using 18.8 mg of aluminum oxide as a reference and the change in calorie during heating was measured with a differential scanning calorimeter (DSC). An exothermic reaction was observed from about 120° C. and the decomposition of the complex was confirmed. FIG. 22 shows the results.

EXAMPLE 10

Production of Ruthenium-containing Thin Film by the CVD Method Using carbonylbis(2-methyl-1,3-pentadiene)ruthenium as Precursor Using a CVD apparatus shown in FIG. 1, film-formation was performed for 1 hour on a silicone wafer provided with an SiO$_2$ film with the use of carbonylbis(2-methyl-1,3-pentadiene)ruthenium as the precursor at a precursor temperature of 50° C., a carrier gas (N$_2$) flow rate of 100 sccm, a precursor pressure of 400 Torr, a counter gas (N$_2$) flow rate of 200 sccm, a pipe temperature of 80° C., a substrate temperature of 300° C., a chamber pressure of 10 Torr and an oxidation gas (O$_2$) flow rate of 300 sccm. By analyzing X-ray diffractometry, it was found out that the film was composed of RuO$_2$. The film thickness measured by SEM was 500 nm.

EXAMPLE 11

Production of Ruthenium-containing Thin Film by the Spin Coating Method Using carbonylbis(2-methyl-1,3-pentadiene)ruthenium as Precursor A solution was prepared by dissolving 1 ml of carbonylbis (2-methyl-1,3-pentadiene)ruthenium in 9 ml of heptane. This solution was spin-coated on a silicone wafer at 500 rpm for 5 seconds and at 1000 rpm for 10 seconds followed by heating in an oven at 150° C. for 20 minutes. By analyzing X-ray diffractometry, it was found out that the film was composed of RuO$_2$. The film thickness measured by SEM was 300 nm.

Comparative Example 4

Film-formation was performed as in Example 10 but starting with bis(ethylcyclopentadienyl)ruthenium. As a result, no ruthenium-containing film could be obtained.

EXAMPLE 12

8.0 g of zinc was introduced into a Schlenk tube. After purging the container with argon, 240 μl of ethylcyclopentadiene and 4 ml of 2,4-dimethyl-1,3-pentadiene were added thereto. Under ice-cooling, a solution of 608 mg of ruthenium chloride n-hydrate (n: about 3) dissolved in 25 ml of dry ethanol was dropped thereinto over 1 hour and 15 minutes. Subsequently, the resultant mixture was stirred under ice-cooling for 1 hour and 30 minutes and then at room temperature for 1 hour. After the completion of the reaction, the unreacted zinc was removed with the use of a glass filter and the residue was concentrated under reduced pressure to give a pasty product. This pasty product was extracted with pentane and the extract was subjected to column chromatography (pentane/alumina) to thereby give 106 mg of the target (2,4-dimethylpentadienyl) (ethylcyclopentadienyl)ruthenium (yield: 16%). Also, 70 mg of bis(ethylcyclopentadienyl)ruthenium was obtained as a by-product (yield: 11%).

While the invention has been described in detail and with reference to specific embodiments thereof, it will be apparent to one skilled in the art that various changes and modifications can be made therein without departing from the spirit and scope thereof.

What is claimed is:

1. A half-sandwich organometallic ruthenium compound represented by the following general formula (1):

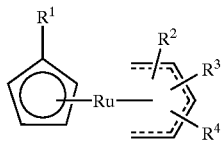

(1)

wherein $R^1$, $R^2$, $R^3$ and $R^4$ are the same or different and each represents hydrogen, a halogen atom, a lower acyl group, a lower alkoxy group, a lower alkoxycarbonyl group or a lower alkyl group, provided that the case where $R^1$ to $R^4$ are all hydrogen, and the case where $R^1$ is hydrogen, one of $R^2$ to $R^4$ is hydrogen, and the remainder are methyl groups are excluded.

2. The half-sandwich organometallic ruthenium compound according to claim 1, wherein said half-sandwich organometallic ruthenium compound is represented by the following general formula (2):

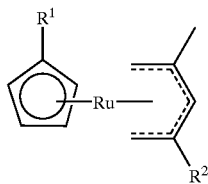

(2)

wherein $R^1$ and $R^2$ are the same or different and each represents hydrogen, a halogen atom, a lower acyl group, a lower alkoxy group, a lower alkoxycarbonyl group or a lower alkyl group, provided that the case where $R^1$ is hydrogen and $R^2$ is a methyl group is excluded.

3. A process for producing a ruthenium-containing thin film which comprises using the half-sandwich organometallic ruthenium compound according to claim 1 as the precursor and forming a ruthenium-containing thin film on a heated substrate by the chemical vapor deposition method.

4. A process for producing a half-sandwich organometallic ruthenium compound represented by the following general formula (1):

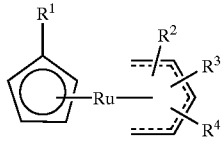

(1)

wherein $R^1$ to $R^4$ are the same or different and each represents hydrogen, a halogen atom, a lower acyl group, a lower alkoxy group, a lower alkoxycarbonyl group or a lower alkyl group, which comprises reacting an open rutenocene represented by the following general formula (3):

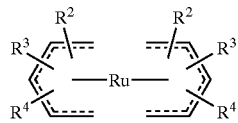

(3)

wherein $R^2$, $R^3$ and $R^4$ are each as defined above; in a solvent in the presence of zinc with a cyclopentadiene represented by the following general formula (4):

(4)

wherein $R^1$ is described above.

5. The process for producing a half-sandwich organometallic ruthenium compound according to claim 4, wherein the open rutenocene represented by the general formula (3) is one obtained by dropping to a liquid mixture of a pentadiene represented by the following general formula (5) with zinc:

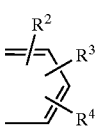

(5)

wherein $R^2$, $R^3$ and $R^4$ are the same or different and each represents hydrogen, a halogen atom, a lower acyl group, a lower alkoxy group, a lower alkoxycarbonyl group or a lower alkyl group;

a solution of a halogenated ruthenium hydrate represented by the following general formula (6):

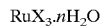

$RuX_3 \cdot nH_2O$ (6)

wherein X represents a halogen atom; and n is a number of from 0 to 10;

diluted with a solvent and reacting therewith.

6. The process for producing a half-sandwich organometallic ruthenium compound according to claim 4, wherein methanol is employed as the whole solvent or a part thereof and, after filtering off the excessive zinc after the completion of the reaction, the ruthenium complex represented by the general formula (1) is extracted with the use of a solvent arbitrarily immiscible with methanol.

7. The process for producing a half-sandwich organometallic ruthenium compound according to claim 4, wherein, after the extraction with the use of a solvent arbitrarily immiscible with methanol, the solution is concentrated and then distilled to thereby purify the half-sandwich organometallic ruthenium compound represented by the general formula (1).

8. The process for producing a half-sandwich organometallic ruthenium compound according to claim 5, wherein the pentadiene represented by the general formula (5) is added in an amount of from 2 to 20 mol per mol of the halogenated ruthenium hydrate.

9. The process for producing a half-sandwich organometallic ruthenium compound according to claim 4, wherein zinc is added in an amount of from 1.5 to 100 mol per mol of the halogenated ruthenium hydrate or the open ruthenocene represented by the general formula (3).

10. The process for producing a half-sandwich organometallic ruthenium compound according to claim 4, wherein the reaction of the pentadiene represented by the general formula (5) with the halogenated ruthenium hydrate represented by the general formula (6) to synthesize the open ruthenocene represented by the general formula (3) is carried out at a temperature of from −20 to 100° C.

11. The process for producing a half-sandwich organometallic ruthenium compound according to claim 4, wherein the reaction of the open ruthenocene represented by the general formula (3) with the cyclopentadiene represented by the general formula (4) to synthesize the half-sandwich organometallic ruthenium compound represented by the general formula (1) is carried out at a temperature of from −20 to 100° C.

12. The process for producing a half-sandwich organometallic ruthenium compound according to claim 4, wherein, in the synthesis of the half-sandwich organometallic ruthenium complex represented by the general formula (1) by reacting the open ruthenocene represented by the general formula (3) with the cyclopentadiene represented by the general formula (4), the cyclopentadiene represented by the general formula (4) is added in an amount of from 0.8 to 1 mol per mol of the open ruthenocene represented by the general formula (3).

13. The process for producing a half-sandwich organometallic ruthenium compound according to claim 4, wherein, after producing the open ruthenocene represented by the general formula (3), it is not isolated but reacted with the cyclopentadiene represented by the general formula (4) in a single pot to thereby synthesize the half-sandwich organometallic ruthenium compound represented by the general formula (1).

14. The process for producing a half-sandwich organometallic ruthenium compound according to claim 4, wherein the reaction is carried out in nitrogen gas or an inert gas atmosphere.

15. The process for producing a ruthenium-containing thin film according to claim 3, wherein a half-sandwich organometallic ruthenium compound solution prepared by dissolving a half-sandwich organometallic ruthenium compound according to claim 1 in an organic solvent is used.

16. A carbonylbis(diene)ruthenium complex represented by the following general formula (7):

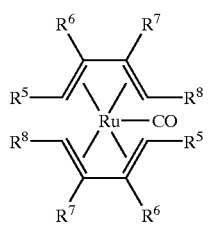

(7)

wherein $R^5$ to $R^8$ represent each hydrogen, an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 to 6 carbon atoms, provided that the case where $R^5$ to $R^8$ are all hydrogen, and the case where $R^5$ and $R^8$ are hydrogen and $R^6$ and $R^7$ are methyl are excluded.

17. The carbonylbis(diene)ruthenium complex according to claim 16, wherein, in the general formula (7), at least one of $R^5$ to $R^8$ is an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 or 2 carbon atoms while the remainder are hydrogen, provided that the case where $R^5$ to $R^8$ are all hydrogen, and the case where $R^5$ and $R^8$ are hydrogen and $R^6$ and $R^7$ are methyl are excluded.

18. The carbonylbis(diene)ruthenium complex according to claim 16, wherein, in the general formula (7), $R^5$ and $R^7$ are hydrogen while $R^6$ and $R^8$ are methyl groups.

19. The process for producing a carbonylbis(diene) ruthenium complex according to claim 16, wherein a ruthenium chloride n-hydrate, wherein n is a number of 1 or more, is reacted with a diene in an alcohol in the presence of a zinc powder.

20. The process for producing a carbonylbis(diene) ruthenium complex according to claim 19, wherein the diene is represented by the following general formula (8):

(8)

wherein $R^5$ to $R^8$ represent each hydrogen, an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 to 6 carbon atoms, provided that the case where $R^5$ to $R^8$ are all hydrogen, and the case where $R^5$ and $R^8$ are hydrogen and $R^6$ and $R^7$ are methyl are excluded.

21. The process for producing a carbonylbis(diene) ruthenium complex according to claim 20, wherein, in the general formula (8), at least one of $R^5$ to $R^8$ is an alkyl group, or an alkyl group containing an alkoxy group, an alkoxycarbonyl group, an alkanoyl group, a hydroxyl group, a carbonyl group, a halogen atom, a carboxyl group, an amino group or a carbamoyl group, and the unsubstituted alkyl group and the substituted alkyl group each has 1 or 2 carbon atoms while the remainder are hydrogen, provided that the case where $R^5$ to $R^8$ are all hydrogen, and the case where $R^5$ and $R^8$ are hydrogen and $R^6$ and $R^7$ are methyl are excluded.

22. The process for producing a carbonylbis(diene) ruthenium complex according to claim 20, wherein, in the general formula (8), $R^5$ and $R^7$ are hydrogen while $R^6$ and $R^8$ are methyl groups.

23. The process for producing a carbonylbis(diene) ruthenium complex according to claim 19, wherein an alcoholic solution of the ruthenium chloride n-hydrate is dropped into the diene or an alcoholic solution of diene having a zinc powder dispersed therein and then reacted at 0 to 80° C.

24. A process for producing a ruthenium-containing thin film which comprises using a carbonylbis(diene)ruthenium complex according to claim 16 as the precursor.

25. The process for producing a ruthenium-containing thin film according to claim 24, wherein ruthenium or ruthenium oxide is grown on a substrate by the chemical vapor deposition method.

26. The process for producing a ruthenium-containing thin film according to claim 24, wherein ruthenium or ruthenium oxide is formed on a substrate by the coating heat decomposition method.

* * * * *